US009784738B2

(12) United States Patent
Gau

(10) Patent No.: US 9,784,738 B2
(45) Date of Patent: Oct. 10, 2017

(54) MODULAR CARTRIDGE FOR LIQUID TRANSPORT

(75) Inventor: Jen-Jr Gau, Pasadena, CA (US)

(73) Assignee: GeneFluidics, Inc., Irwindale, CA (US)

( * ) Notice: Subject to any disclaimer, the term of this patent is extended or adjusted under 35 U.S.C. 154(b) by 1133 days.

(21) Appl. No.: 12/931,048

(22) Filed: Jan. 22, 2011

(65) Prior Publication Data

US 2011/0220656 A1 Sep. 15, 2011

Related U.S. Application Data

(60) Provisional application No. 61/336,490, filed on Jan. 23, 2010.

(51) Int. Cl.
*G01N 33/543* (2006.01)
*B01L 3/00* (2006.01)

(52) U.S. Cl.
CPC .... *G01N 33/5438* (2013.01); *B01L 3/502715* (2013.01); *B01L 3/502707* (2013.01); *B01L 2200/025* (2013.01); *B01L 2200/027* (2013.01); *B01L 2200/028* (2013.01); *B01L 2200/0689* (2013.01); *B01L 2300/0645* (2013.01); *B01L 2300/0816* (2013.01); *B01L 2400/0481* (2013.01); *B01L 2400/0638* (2013.01); *Y10T 29/49815* (2015.01)

(58) Field of Classification Search
CPC ......... B01L 2200/025; B01L 2200/027; B01L 2200/28
See application file for complete search history.

(56) References Cited

U.S. PATENT DOCUMENTS

| 4,683,159 | A | * | 7/1987 | Bohrer et al. | 428/138 |
| 7,192,559 | B2 | * | 3/2007 | Chow et al. | 422/504 |
| 7,476,360 | B2 | * | 1/2009 | Gau et al. | 422/504 |
| 7,641,856 | B2 | * | 1/2010 | Padmanabhan et al. | 422/73 |
| 2004/0087008 | A1 | | 5/2004 | Schembri | |
| 2004/0109793 | A1 | * | 6/2004 | McNeely et al. | 422/100 |
| 2005/0196855 | A1 | * | 9/2005 | Gau et al. | 435/287.2 |
| 2005/0205136 | A1 | | 9/2005 | Freeman | |
| 2007/0053796 | A1 | * | 3/2007 | Gau et al. | 422/100 |
| 2008/0200343 | A1 | | 8/2008 | Clemens et al. | |
| 2008/0216736 | A1 | | 9/2008 | David | |

OTHER PUBLICATIONS

Lindner, Nora, International Preliminary Report on Patentability and Written Opinion, PCT/US11/00122, The International Bureau of WIPO, Aug. 2, 2012.
Young, Lee W., International Search Report and Written Opinion, PCT/US11/00122, United States Patent and Trademark Office, May 26, 2011.

* cited by examiner

*Primary Examiner* — Sam P Siefke
(74) *Attorney, Agent, or Firm* — Gavrilovich, Dodd & Lindsey, LLP

(57) ABSTRACT

A device includes multiple components that are independent from one another but are configured to be detachably coupled with one another so as to form a cartridge. One of the components is a clamp that is configured to hold the other components such that they are coupled together. The cartridge has one or more reservoirs, one or more functional chambers, and one or more channels configured to transport a liquid stored in at least one of the one or more reservoirs into the one or more functional chambers.

20 Claims, 10 Drawing Sheets

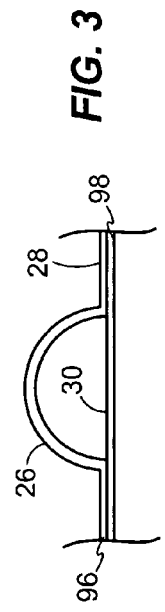
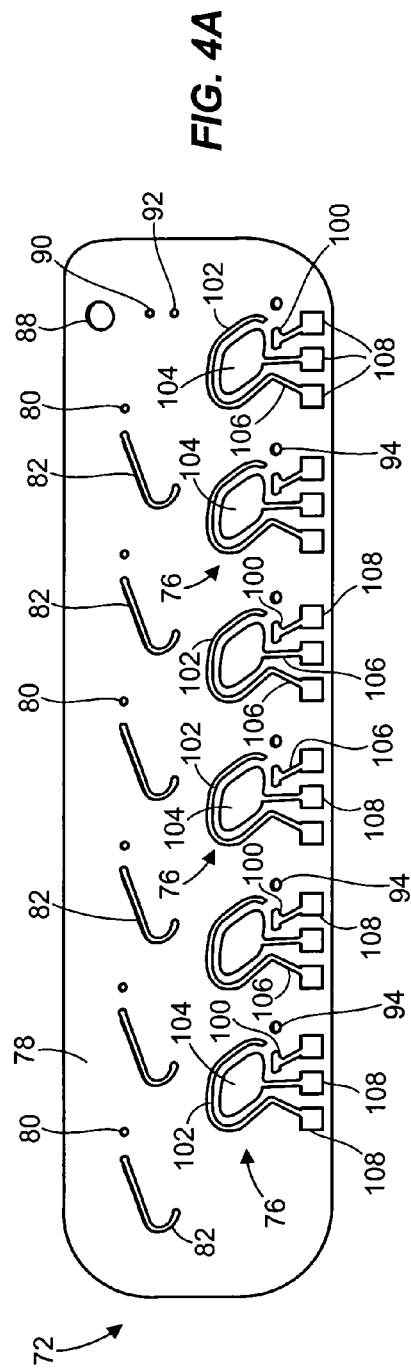
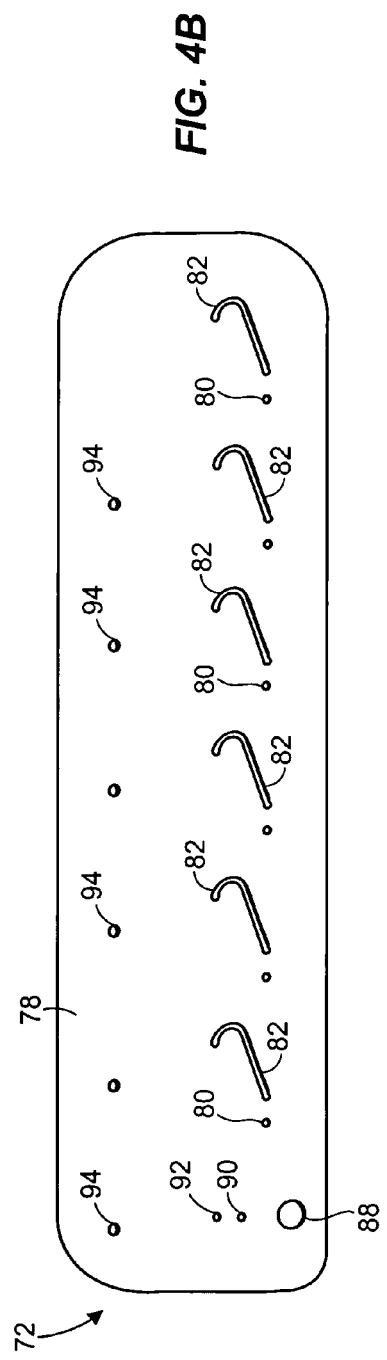
FIG. 3
FIG. 4A
FIG. 4B

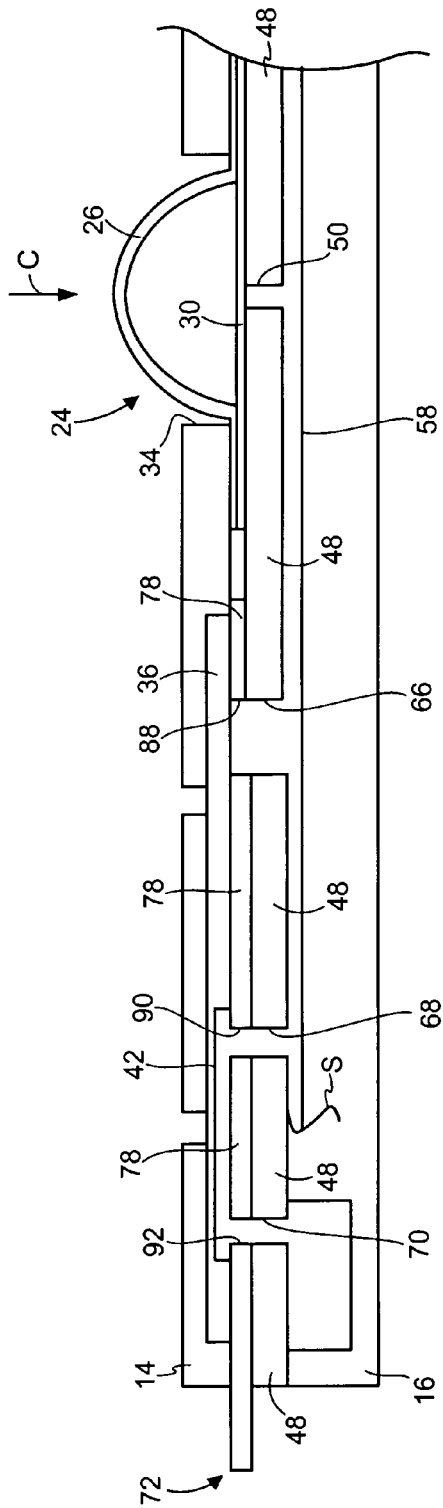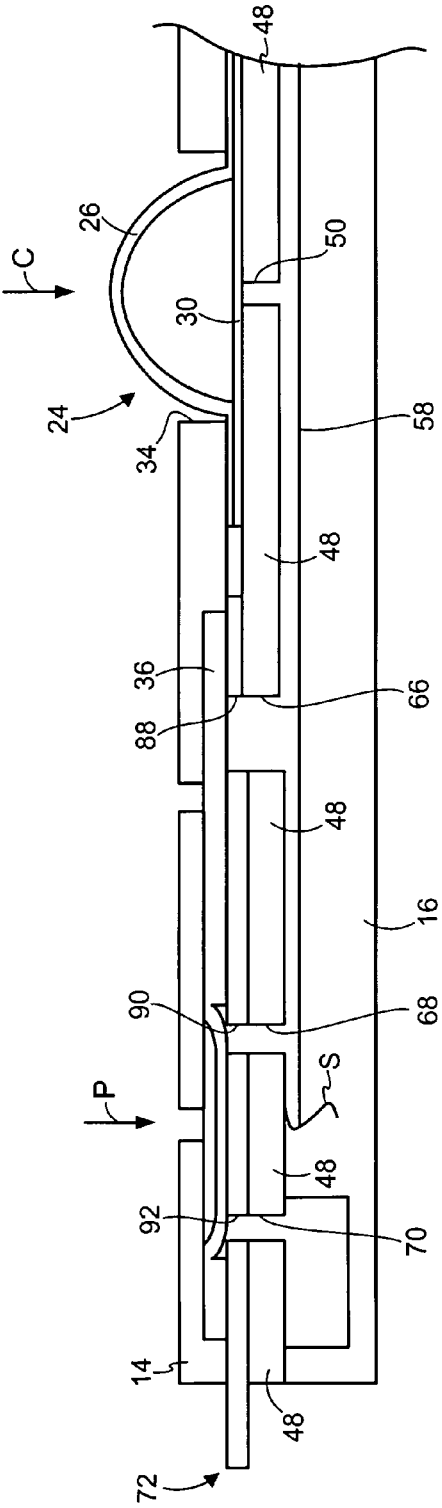
FIG. 8A
FIG. 8B

MODULAR CARTRIDGE FOR LIQUID TRANSPORT

RELATED APPLICATIONS

This Application claims the benefit of U.S. Provisional Patent Application Ser. No. 61/336,490, filed on Jan. 23, 2010, entitled "Modular Cartridge for Liquid Transport," and incorporated herein in its entirety.

FIELD

The invention relates to liquid transport systems and more particularly to systems for delivery of a liquid to a sensor.

BACKGROUND

A variety of assays can be performed using an assay chip that includes one or more sensors positioned on a substrate. A cartridge can be employed to transport various liquids to the sensors. The cartridge typically includes one or more reservoirs that each holds one of the solutions. During the operation of the cartridge, the cartridge is inserted into a machine that causes the liquids in the reservoirs to be transported to the one or more sensors. The machine can then operate the one or more sensors so as to perform the assay.

SUMMARY

A device includes multiple components that are independent from one another but are configured to be detachably coupled with one another so as to form a cartridge. One of the components is a clamp that is configured to hold the other components such that they are coupled together. The cartridge has one or more reservoirs, one or more functional chambers, one or more sensors positioned in each of the functional chambers, and one or more channels configured to transport a liquid stored in at least one of the one or more reservoirs into the one or more functional chambers.

A system is also disclosed. The system includes multiple components that are independent from one another but are configured to be detachably coupled with one another so as to form a cartridge having one or more reservoirs, one or more functional chambers and one or more channels configured to transport a liquid stored in at least one of the one or more reservoirs into the one or more functional chambers. The components include a clamp configured to hold the other components together. The system also includes multiple first substitute components, each of the first substitute components includes one or more features that are different from features on each of the other first substitute components. Each of the first substitute component are interchangeable in that any one of the first substitute components can serve as a first one of the components.

A system is also disclosed. The system includes a first cartridge having one or more reservoirs and one or more sensors. The first cartridge is configured to transport a liquid from at least one of the reservoirs into contact with the one or more sensors. The first cartridge is constructed from multiple components that are independent from one another but are configured to be detachably coupled with one another so as to form the first cartridge. A second cartridge is formed after at least a portion of the components of the first cartridge are detached from one another. The second cartridge has one or more reservoirs and one or more sensors and is configured to transport a liquid from at least one of the reservoirs into contact with the one or more sensors. The second cartridge is constructed from multiple components that are independent from one another but are configured to be detachably coupled with one another so as to form the second cartridge. Additionally, the second cartridge includes a portion of the components from the first cartridge but also including components that were not included in the first cartridge.

A method is also disclosed. The method includes forming a first cartridge having one or more reservoirs and one or more sensors. The first cartridge is configured to transport a liquid from at least one of the reservoirs into contact with the one or more sensors. The cartridge is formed from multiple components that are independent from one another but are configured to be detachably coupled with one another so as to form the first cartridge. The method also includes detaching at least a portion of the components in the first cartridge and forming a second cartridge. The second cartridge has one or more reservoirs and one or more sensors and is configured to transport a liquid from at least one of the reservoirs into contact with the one or more sensors. The second cartridge is formed constructed from multiple components that are independent from one another but are configured to be detachably coupled with one another so as to form the second cartridge. Additionally, the second cartridge includes a portion of the components from the first cartridge but also includes components that were not included in the first cartridge.

BRIEF DESCRIPTION OF THE FIGURES

FIG. 1A is a perspective view of the cartridge with the clamp in the open position and the various components of the cartridge separated from one another.

FIG. 1B is a perspective view of the cartridge with the clamp in the open position with the components positioned in the positions they would occupy immediately before closure of the clamp or immediately after opening of the clamp.

FIG. 1C illustrates the cartridge of FIG. 1B after closure of the clamp.

FIG. 3 illustrates a suitable construction of a component of the cartridge that includes one or more reservoirs that are each configured to store a liquid to be transported to one or more sensors in the cartridge.

FIG. 4A and FIG. 4B illustrate a suitable construction of a component of the cartridge. The illustrated component is a sensor structure that includes one or more sensors positioned on a substrate. FIG. 4A is a sideview of the sensor structure and FIG. 4B is a sideview of the sensor structure 72 taken looking in the opposite direction of the sideview of FIG. 4A.

FIG. 5A and FIG. 5B are perspective views of a portion of the gasket. FIG. 5A is a perspective view of the gasket. FIG. 5B is a perspective view of the gasket shown in FIG. 5A looking toward a side of the gasket that opposes the side shown in FIG. 5A.

FIG. 6A and FIG. 6B are essentially a cross-section of the cartridge with the clamp in the closed position; however, the cross-section is not taken along a plane but is instead taken along a liquid pathway from a reservoirs to a sensors, and then into a waste reservoir.

FIG. 8A through FIG. 8B illustrate operation of a vent in the cartridge constructed according to FIG. 1A through FIG. 1C. FIG. 8A and FIG. 8B are essentially cross-sections of the cartridge with the clamp in the closed position; however, the cross-section is not taken along a plane but is instead taken along the liquid pathway from one of the reservoirs through the vent, and then into one of the waste reservoirs.

DESCRIPTION

Figure 1A:
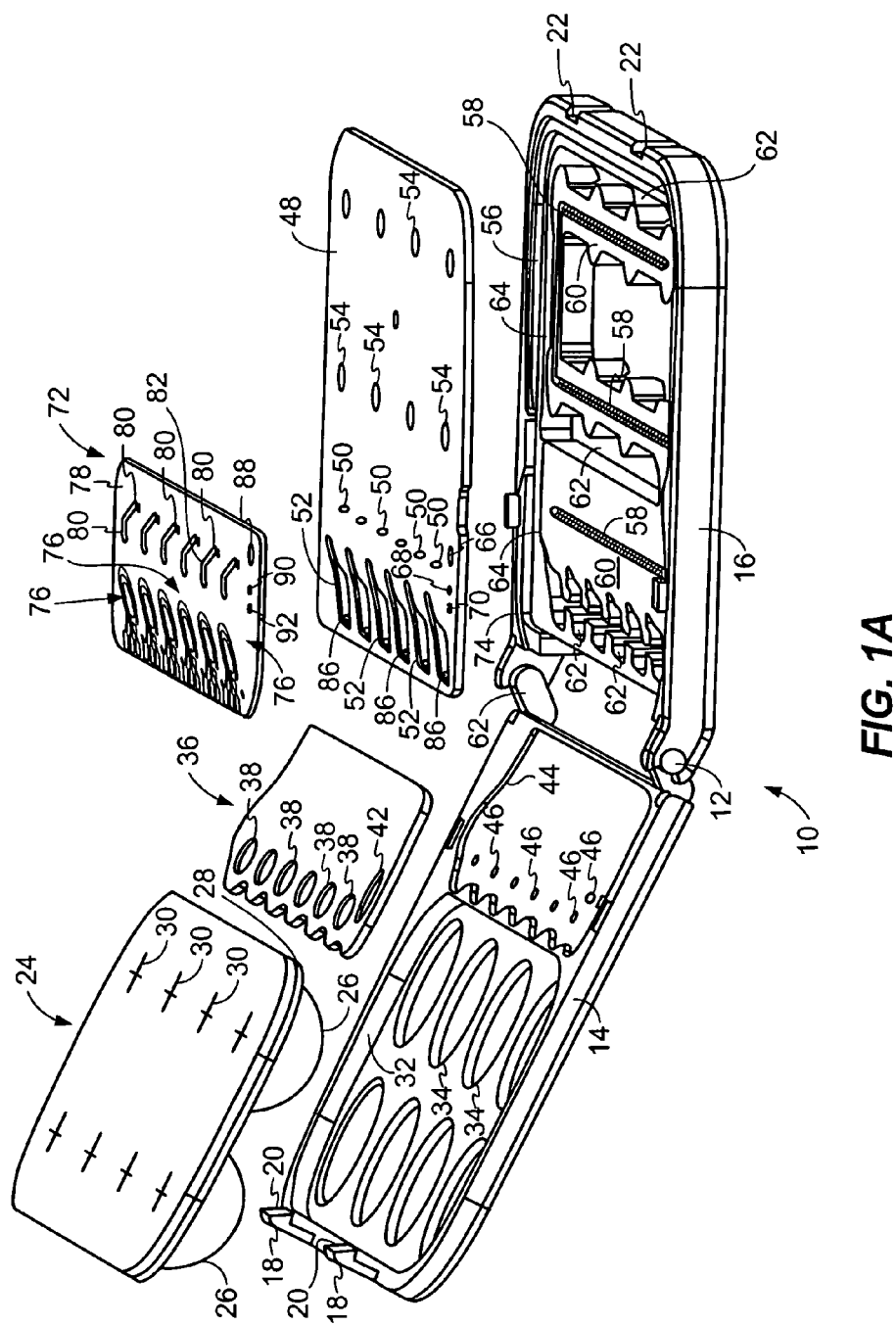
FIG. 1A through FIG. 1C illustrate a cartridge. The cartridge includes multiple components. The components include a clamp that can be positioned in an open position or a closed position. When the clamp is closed, the clamp is configured to immobilize the other components relative to each other.

A cartridge includes multiple components that are independent from one another in that they are not bonded to one another or permanently immobilized relative to one another. The components are configured to be detachably coupled with one another so as to form the cartridge. One of the components is a clamp that holds the other components such that they are coupled together. The clamp can press the other components together and can form one or more liquid seals between adjacent components. Coupling of the components forms the cartridge with one or more reservoirs, and one or more functional chambers, one or more sensors positioned in each of the functional chambers, and one or more channels for transporting liquids stored in the one or more reservoirs into the one or more functional chambers. The cartridge can be inserted into a machine that operates the cartridge. For instance, the machine can cause one or more liquids to be transported from the reservoirs into contact with the one or more sensors so as to form a sample on these sensors and then the machine can operate the sensors so as to gather data from the sensors.

The ability of the components to be detachably coupled together allows one or more components of the cartridge to be replaced in the between subsequent uses of the cartridge. Additionally, the ability of the components to be detachably coupled together allows one or more components of the cartridge to be replaced with a component that has different functionality. Changing the functionality of different components allows the cartridge to be customized to different assays.

The detachability of the components means the components can be separated before and after use of the cartridge. As a result, the operator of the cartridge to access different regions of the cartridge before and after operation of the cartridge. For instance, the one or more sensors can each be an electrochemical sensor. Before using the cartridge, it may be desirable to prepare one or more surfaces of the electrochemical sensor. As an example, it may be desirable to form a coating on one or more electrodes in the electrochemical sensor. Examples of suitable coatings include, but are not limited to, self-assembly monolayers as described in U.S. patent application Ser. No. 09/848,727. Since the components are detachable, it is possible to access the sensor to form this self-assembly monolayer before use of the cartridge. Further, the detachability of the components allows the sensor to be accessed after use of the cartridge. As a result, the self-assembly monolayer to be removed and changed before the cartridge is used another time.

The components of the cartridge are constructed for simple fabrication. For instance, a portion of the components can be fabricated using three-dimensional printing technologies while another portion of the components can be fabricated using computer controlled laser cutting and rasterization. The techniques can allow these components to be both designed and fabricated in less than an hour. As a result, the components of the cartridge can be quickly and easily re-designed to allow the cartridge to perform different functions. For instance, the components of the cartridge can be changed such that the cartridge includes a different number of functional chambers, reservoirs, valves, vents, and/or channels for transporting liquids to and/or from these components. Additionally or alternately, the components of the cartridge can be changed such that the channels provide liquid communication between different features of the cartridge.

Figure 1B:
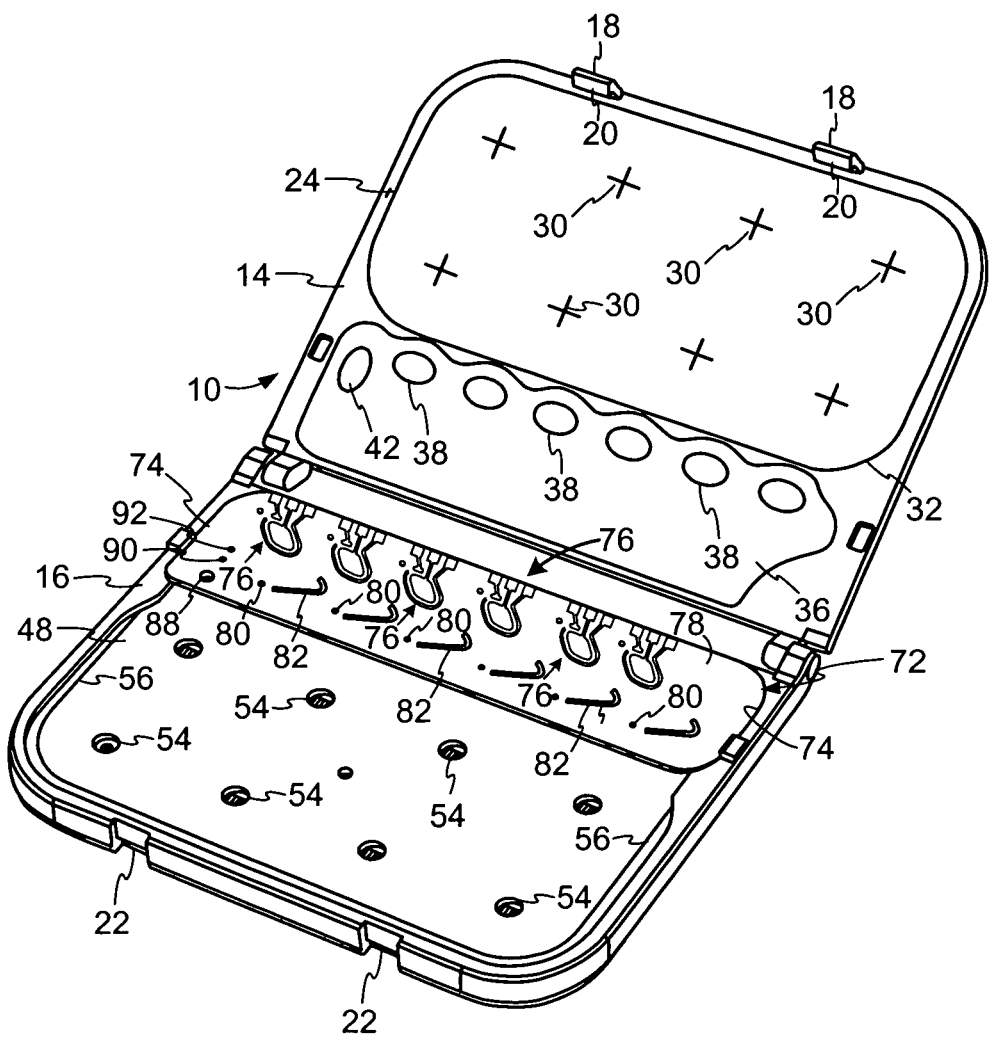
Figure 1C:
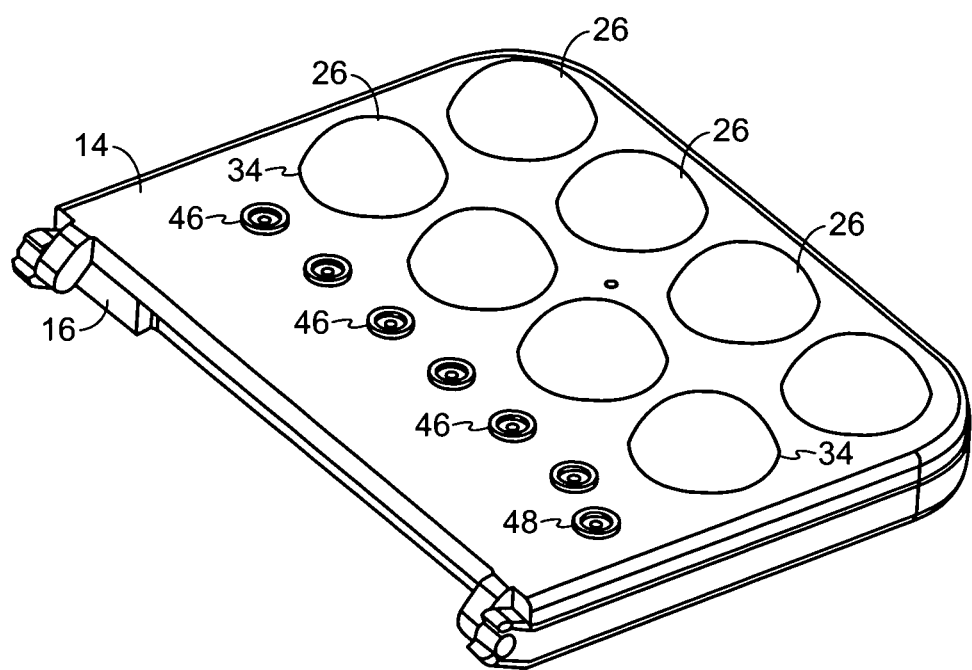

FIG. 1A through FIG. 1C illustrate a cartridge. The cartridge includes multiple components. The components include a clamp 10 that can be positioned in an open position or a closed position. When the clamp 10 is closed, the clamp 10 is configured to immobilize the other components relative to each other. When the clamp 10 is opened, all or a portion of the other components can be moved relative to each other.

FIG. 1A is a perspective view of the cartridge with the clamp 10 in the open position and the various components of the cartridge separated from one another. FIG. 1B is a perspective view of the cartridge with the clamp 10 in the open position but rather than being spaced apart from each other, the components are positioned in the positions they would occupy immediately before closure of the clamp 10 or immediately after opening of the clamp 10. FIG. 1C illustrates the cartridge of FIG. 1B after closure of the clamp 10.

The clamp 10 includes a shell that holds the other components of the cartridge. The shell includes a hinge 12 that allows a first shell 14 to be moved relative to a second shell 16. The clamp 10 includes a holding device configured to hold the clamp 10 in the closed position. For instance, FIG. 1A illustrates the first shell 14 having prongs 18. The prongs 18 each have a protrusion 20 that fits into a recess 22 on the second shell 16. When the protrusions 20 are each fit into one of the recesses 22, the clamp 10 resists opening. In some instances, the holding devices are configured such that once the clamp 10 is closed, the clamp 10 can be re-opened so the clamp 10 and/or the cartridge can be used multiple times. When the clamp 10 is in the closed position, the clamp 10 can compress other components of the cartridge together. As will become evident below, the level of compression can be such that a liquid seal is formed between adjacent components.

The components of the cartridge include a reservoir member 24 that includes multiple pockets 26 that each extends from a side of a common platform 28. Each of the pockets 26 can define a reservoir in the reservoir member 24. A liquid for performing an assay can be stored in each reservoir or in a portion of the reservoirs. Each reservoir is partially defined by a septum 30 that provides a liquid passageway through which a liquid within the reservoir can flow. Additionally or alternately, a pipette or other device can be used to transport a liquid into the reservoir through the septum 30 for that reservoir.

A reservoir member recess 32 extends into the first shell 14. The reservoir member recess 32 is configured to receive the common platform 28 of the reservoir member 24 such that lateral movement of the common platform 28 relative to the first shell 14 is limited. The first shell 14 includes pocket openings 34 that each extends through the bottom of the reservoir member recess 32. The pocket openings 34 are each configured to receive one of the pockets 26. When the clamp 10 is in the closed position, the common platform 28 is positioned within the clamp 10 with each pocket 26 extending through one of the pocket openings 34. Additionally, upon closure of the clamp 10, the bottom of the reservoir member recess 32 can be in contact with the common platform 28 of the reservoir member 24 and/or press against the common platform 28 of the reservoir member 24 so as to compress the other components of the cartridge against one another.

The components of the cartridge include a first gasket 36. The first gasket 36 includes valve recesses 38 that extend part way into a common region. The first gasket 36 also includes a vent recess 42 that extends part way into the common region. The first shell 14 includes a first gasket recess 44 configured to receive the first gasket 36 such that lateral movement of the first gasket 36 relative to the first shell 14 is limited. The first shell 14 includes valve actuation openings 46 that each extends from the bottom of the first gasket recess 44 through the first shell 14. When the first gasket 36 is received in the first gasket recess 44, the valve actuation openings 46 are each aligned with a different one of the valve recesses 38 and with the vent recess 42. Upon closure of the clamp 10, the bottom of the first gasket recess 44 can be in contact with the first gasket 36 and/or press against the first gasket 36 against other components in the cartridge.

The components of the cartridge include a second gasket 48. The second gasket 48 includes valve openings 50 that each extends through the second gasket 48. The second gasket 48 includes chamber recesses 52 that each extends part way into the second gasket 48. The second gasket 48 includes reservoir openings 54 that each extends through the second gasket 48. Upon closure of the clamp 10, each of the reservoir openings 54 aligns with a liquid passageway from one of the reservoirs. Additionally, the components of the cartridge are configured such that upon closing of the clamp 10, the common platform 28 of the reservoir member 24 is pressed against the second gasket 48 so as to create a liquid seal between second gasket 48 and the common platform 28 of the reservoir member 24. As a result, liquid that flows out of a reservoir flows through the aligned reservoir opening 54. Accordingly, each reservoir opening 54 is associated with one of the reservoirs.

The second shell 16 includes a second gasket recess 56 configured to receive the second gasket 48 such that lateral movement of the second gasket 48 relative to the second shell 16 is limited.

The second shell 16 includes a common channel 58 that extends part way into a surface 60 of the second shell 16. Upon receipt of the second gasket 48 in the second gasket recess 56, each of the reservoir openings 54 in the second gasket 48 aligns with the common channel 58 such that a liquid in one of the reservoirs can flow out of the reservoir and through the aligned reservoir opening 54 and into the common channel 58. The components of the cartridge are configured such that upon closing of the clamp 10, the second gasket 48 is pressed against the surface 60 of the second shell 16 so as to create a liquid seal between the second gasket 48 and the surface 60 of the second shell 16. As a result, liquid transported into the common channel 58 flows through the common channel 58. Additionally, upon receipt of the second gasket 48 in the second gasket recess 56, each of the valve openings 50 in the second gasket 48 aligns with the common channel 58 such that a liquid flowing in the common channel 58 can flow into each of the valve openings 50.

The second shell 16 also includes waste reservoirs 62 that each extends part way into the surface 60 of the second shell 16. Waste channels 64 can provide hydraulic communication between different waste reservoirs 62. Accordingly, the waste reservoirs 62 can effectively merge into a single waste reservoir 62.

The second gasket 48 also includes a gas opening 66, a vent inlet opening 68, and a vent outlet opening 70 that each extends through the second gasket 48. Upon receipt of the second gasket 48 in the second gasket recess 56, the gas opening 66 aligns with the common channel 58. As will be described in more detail below, when there is a gas in the common channel 58, the gas can flow into the gas opening 66. Upon receipt of the second gasket 48 in the second gasket recess 56, the vent inlet opening 68 aligns with the common channel 58. As a result, a liquid in the common channel 58 can flow into the vent inlet opening 68. Further, upon receipt of the second gasket 48 in the second gasket recess 56, the vent outlet opening 70 aligns with a waste reservoir 62 in the second shell 16.

The components of the cartridge include a sensor structure 72. The second shell 16 includes a sensor recess 74. The sensor recess 74 is configured to receive the sensor structure 72 such that lateral movement of the sensor structure 72 relative to the second shell 16 is limited.

The sensor structure 72 includes one or more sensors 76 on a substrate 78. Suitable sensors 76 include, but are not limited to, electrochemical sensors, impedance sensors, and electrochemiluminescence sensors. In a preferred example, the sensor 76 is an electrochemical sensor. A suitable electrochemical sensor employs electrical energy to cause a chemical reaction that changes one or more compounds in a liquid that contacts the sensor 76 into another compound. Examples of reactions include redox reactions. Electrochemical sensors can be employed in methods such as cyclic voltammetry.

In FIG. 1A through FIG. 1C, the substrate 78 is treated as transparent and can be transparent in reality. The sensors of FIG. 1A through FIG. 1C are positioned on the underside of the substrate 78 but are visible due to the treatment of the substrate 78 as transparent. Suitable materials for the substrate 78 include, but are not limited to, acrylics, polyesters (PET), polyethylene-terephthalate glycol (PETG), polycarbonates, and thermoplastics.

The sensor structure 72 includes secondary valve conduits 80 that each extends through the substrate 78. Upon receipt of the sensor structure 72 in the sensor recess 74, the secondary valve conduits 80 each align with one of the valve openings 50 in the second gasket 48. Additionally, the components of the cartridge are configured such that upon closing of the clamp 10, the substrate 78 of the sensor structure 72 are pressed against the second gasket 48 so as to create a liquid seal between second gasket 48 and the substrate 78 of the sensor structure. As a result, a liquid that flows from the common channel 58 and into a valve opening 50 in the second gasket 48 can then flow into the secondary valve conduit 80 that is aligned with that valve opening 50.

Additionally, upon closure of the clamp 10, the valve recesses 38 in the first gasket 36 each align with one of the secondary valve conduits 80 in the sensor structure 72. The components of the cartridge are configured such that upon closing of the clamp 10, the substrate 78 of the sensor structure 72 are pressed against the first gasket 36 so as to create a liquid seal between first gasket 36 and the substrate 78 of the sensors structure. As a result, a liquid in a secondary valve conduit 80 can flow into the valve recess 38 that is aligned with that secondary valve conduit 80.

The substrate 78 also includes sensor specific channels 82 that each extends through the substrate 78. Upon closure of the clamp 10, an end of each sensor specific channel 82 aligns with a different one of the valve recesses 38 in the first gasket 36. Accordingly, each valve recess 38 can span one of the secondary valve conduits 80 in the substrate 78 and one of the sensor specific channels 82 in the substrate 78. As a result, a liquid in one of the secondary valve conduits 80 can flow through the associated valve recess 38 and then into the associated sensor specific channel 82.

Upon closure of the clamp 10, an end of each sensor specific channel 82 aligns with a different one of the chamber recesses 52 in the second gasket 48. Accordingly, a liquid in one of the sensor specific channels 82 can flow into the aligned chamber recesses 52. Each of the chamber recesses 52 defines a portion of an functional chamber in the cartridge. The substrate 78 of the sensor structure 72 defines another portion of each of the functional chambers. Further, the sensors 76 are positioned on the substrate 78 such that upon closure of the clamp 10, each sensor 76 is positioned in one of the functional chambers. As a result, a liquid that flows from one of the sensor specific channels 82 into the aligned chamber recess 52 flows into one of the functional chambers and accordingly into contact with the sensor 76 located in that functional chamber.

The second gasket 48 includes waste openings 86 that each extends from a bottom of the chamber recess 52 through the second gasket 48. Upon closure of the clamp 10, each of the waste recesses aligns with a waste reservoir 62 in the second shell 16. As a result, a liquid in an functional chamber can flow through a waste opening 86 into a waste reservoir 62.

The sensor structure 72 includes a secondary gas opening 88, a secondary vent inlet opening 90, and a secondary vent outlet opening 92 that each extends through the substrate 78. Upon receipt of the sensor structure 72 in the sensor recess 74, the secondary gas opening 88 aligns with the gas opening 66 in the second gasket 48. As will be described in more detail below, when there is a gas in the common channel 58, the gas can flow through the gas opening 66 in the second gasket 48 and into the secondary gas opening 88 in the sensor structure 72. Upon receipt of the sensor structure 72 in the sensor recess 74, the secondary vent inlet opening 90 aligns with the vent inlet opening 68 in the second gasket 48. As a result, a liquid in the common channel 58 can flow through the vent inlet opening 68 in the second gasket 48 and into the secondary vent inlet opening 90 in the sensor structure 72.

Upon closure of the clamp 10, the secondary vent inlet opening 90 and the secondary vent outlet opening 92 aligns with the vent recess 42 in the first gasket 36 such that the vent recess 42 spans the secondary vent inlet opening 90 and the secondary vent outlet opening 92. As a result, a liquid flowing through the secondary vent inlet openings 90 can flow through the vent recess 42 and into the secondary vent outlet opening 92. The liquid flowing through the secondary vent outlet openings 92 can flow through the aligned vent outlet opening 70 and then into the aligned waste reservoir 62.

Figure 2:
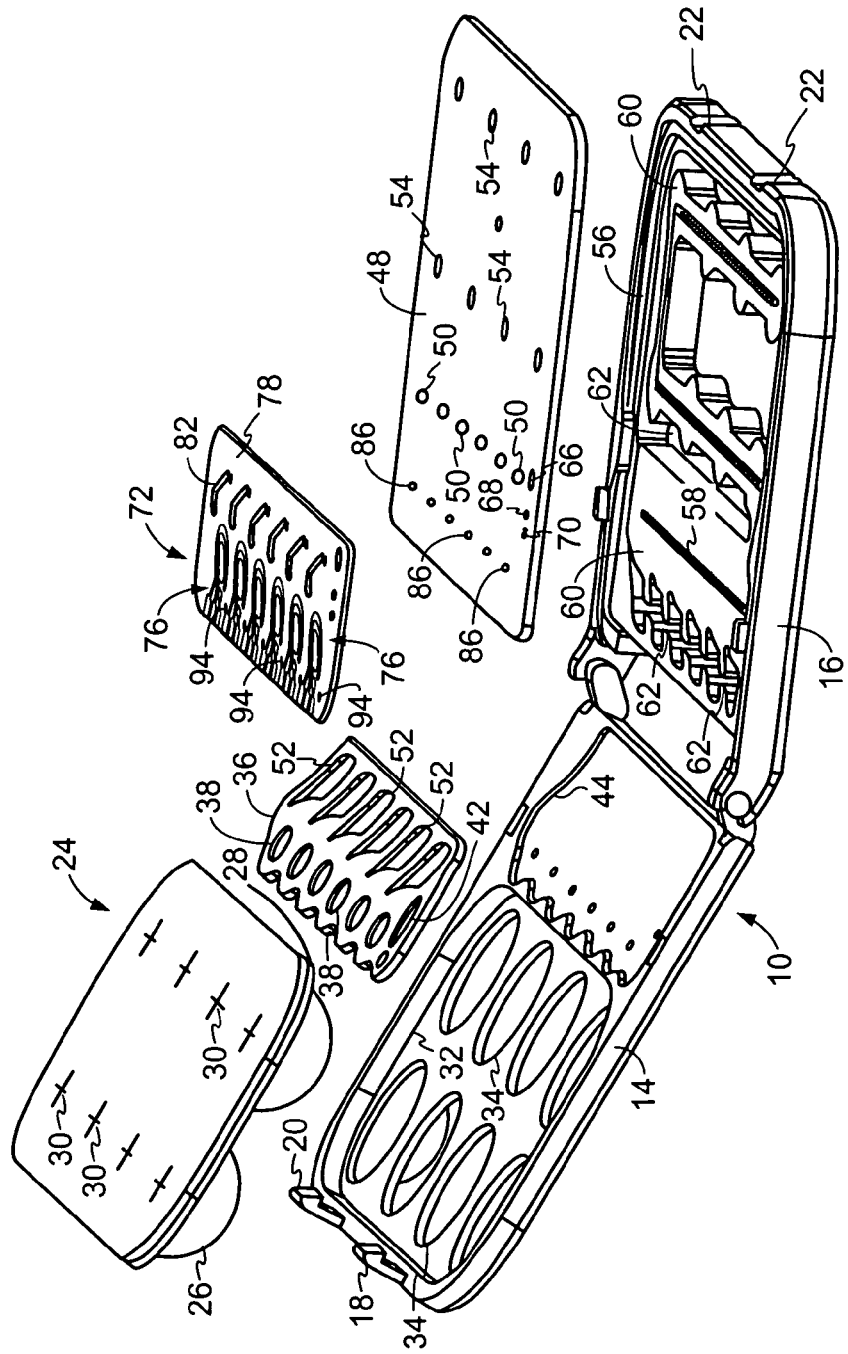
FIG. 2 illustrates another possible arrangement for the features on the components in the cartridge of FIG. 1A through FIG. 1C.

The components can have other arrangements. For instance, FIG. 2 illustrates the cartridge of FIG. 1A through FIG. 1C having the chamber recesses 52 positioned on the first gasket 36 rather than on the second gasket 48. Additionally, the sensors 76 are positioned on the topside of the substrate 78 rather then the underside of the substrate 78 as in FIG. 1A and FIG. 1B. Upon closure of the clamp 10, an end of each sensor specific channel 82 aligns with a different one of the chamber recesses 52 in the first gasket 36. Accordingly, a liquid in one of the sensor specific channels 82 can flow into the aligned chamber recesses 52. Each of the chamber recesses 52 defines a portion of an functional chamber in the cartridge. The substrate 78 of the sensor structure 72 defines another portion of each of the functional chambers. Further, the sensors 76 are positioned on the substrate 78 such that upon closure of the clamp 10, each sensor 76 is positioned in one of the chamber recesses 52 and accordingly in each of the functional chambers. As a result, a liquid that flows from one of the sensor specific channels 82 into the aligned chamber recess 52 flows into one of the functional chambers and accordingly into contact with the sensor 76 located in that functional chamber.

The sensor structure 72 of FIG. 2 includes waste conduits 94 that each extends through the substrate 78. Each of the waste conduits 94 is positioned such that upon closure of the clamp 10, each of the waste conduits 94 is positioned in a different one of the chamber recesses 52 and is also aligned with one of the waste openings 86 included in the second gasket 48. As a result, a liquid in an functional chamber can flow through the waste conduit 94 in the functional chamber, through the aligned waste opening 86 in the second gasket 48 and into a waste reservoir 62.

FIG. 3 illustrates a suitable construction of a suitable reservoir member 24. The reservoir member 24 includes a pocket layer 96 and a septum layer 98. The pocket layer 96 includes one or more pockets 26 extending from the common platform 28. Suitable materials for the pocket layer 96 include, but are not limited to, silicone, thermoplastic elastomers (TPE), and polyurethane. The pocket layer 96 can be formed by methods such as casting, injection molding, and thermoforming.

A single septum layer 98 can extend across the opening of a single pocket 26 or across the opening of multiple pocket layers 96. Accordingly, the reservoir member 24 can include multiple septum layers 98. Suitable materials for the septum layer 98 include, but are not limited to, silicone, thermoplastic elastomers (TPE), and polyurethane. A septum layer 98 can be attached to the pocket layer 96 by methods that include, but are not limited to, adhesive bonding, thermo-bonding, and clamping.

FIG. 4A and FIG. 4B illustrates a sensor structure 72 that is suitable for use with the cartridge. FIG. 4A is a sideview of the sensor structure 72. FIG. 4B is a sideview of the sensor structure 72 taken looking in the opposite direction of the sideview of FIG. 4A. The sensor structure 72 includes a plurality of electrodes positioned on a substrate 78. Suitable materials for the substrate include, but are not limited to, acrylics, polyesters (PET), polyethylene-terephthalate glycol (PETG), polycarbonates, and thermoplastics. Although the substrate 78 is shown as being constructed from a single material, the substrate 78 can have a composite construction.

The electrodes include a reference electrode 100 and a counter electrode 102 positioned adjacent to a working electrode 104. In some instances, each of the electrodes, including the reference electrode 100, is formed from a single layer of an electrically conductive material. Suitable electrically conductive materials, include, but are not limited to, gold. Electrical leads 106 provide electrical communication between each of the electrodes and an electrical contact 108. The sensor structure of FIG. 4A and FIG. 4B can be fabricated using traditional integrated-circuit fabrication techniques. Other sensor constructions are disclosed in U.S. patent application Ser. No. 09/848,727, filed on May 5, 2001, entitled "Biological Identification System with Integrated Sensor Chip and incorporated herein in its entirety.

During operation of one of the sensors 76 to analyze a sample, the sensor 76 is in electrical communication with electronics (not shown) configured to apply a potential between the working electrode 104 and the reference electrode 100 of a sensor 76 while monitoring current passing through a circuit that includes the working electrode 104, a liquid sample positioned on the sensor 76, and the counter electrode 102. The sensor 76 can be employed as an electrochemical sensor. For instance, when analyzing a sample, the potential applied between the working electrode 104 and the reference electrode 100 can be raised to a level that can cause electron transfer to occur between the working electrode 104 and a component in the sample. The electron transfer allows current to flow through the circuit that includes the working electrode 104, the sample and the counter electrode 102. As a result, the sensor can be employed in electrochemical analysis such as voltammetry including cyclic voltammetry. Operation of the sensor so as to detect the presence of an agent is discussed in more detail in U.S. patent application Ser. No. 09/848,727, filed on May 3, 2001, entitled "Biological Identification System with integrated Sensor Chip" and incorporated herein in its entirety.

The sensor structure 72 of FIG. 4A and FIG. 4B includes waste conduits 94 extending through the substrate 78. However, these waste conduits 94 are optional. For instance, the sensor structure 72 of FIG. 2 makes use of these waste conduits 94 but the waste conduits 94 are optional for the cartridge of FIG. 1A through FIG. 1C.

The sensor structure need not include sensors. For instance, the sensor structure can include one or more electrokinetic devices positioned in the functional chambers. Suitable electrokinetic devices includes electrophoretic devices. These devices can include two or more electrodes positioned in the functional chamber. An electrical field can be formed between the electrodes so as to form an electric field in the functional chamber. The electrical field can cause movement of compounds within the functional chamber. A sensor structure that includes one or more electrokinetic devices need not include any sensors or can include the one or more electrokinetic devices in addition to one or more sensors.

Further, in some instances, the functional chamber is empty of devices such as sensors and electrokinetic devices. For instance, a functional chamber without devices can be employed for mixing of liquids or for culturing antibiotics.

Figure 5A:
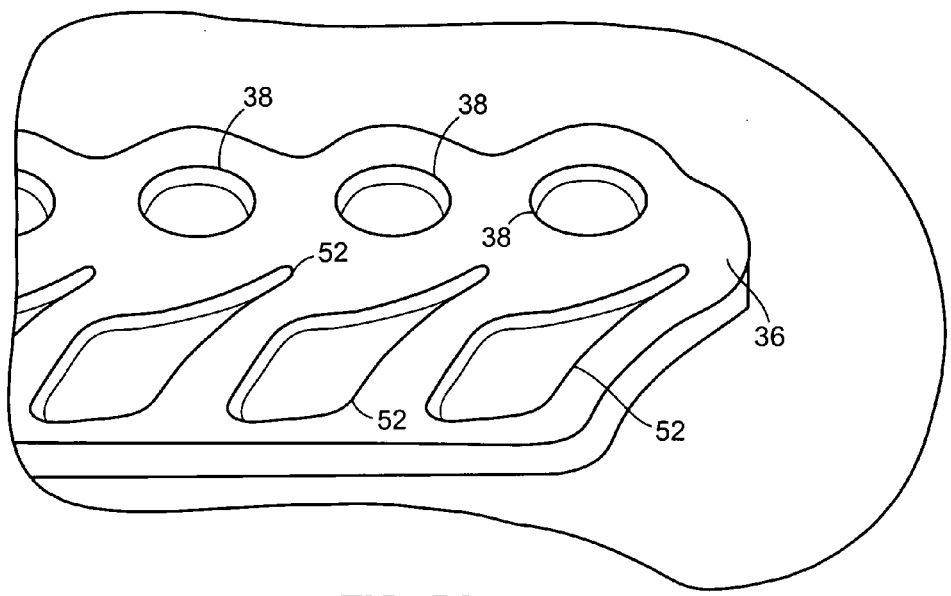
FIG. 5A and FIG. 5B illustrate an example of component of the cartridge. The illustrated component is a gasket.
Figure 5B:
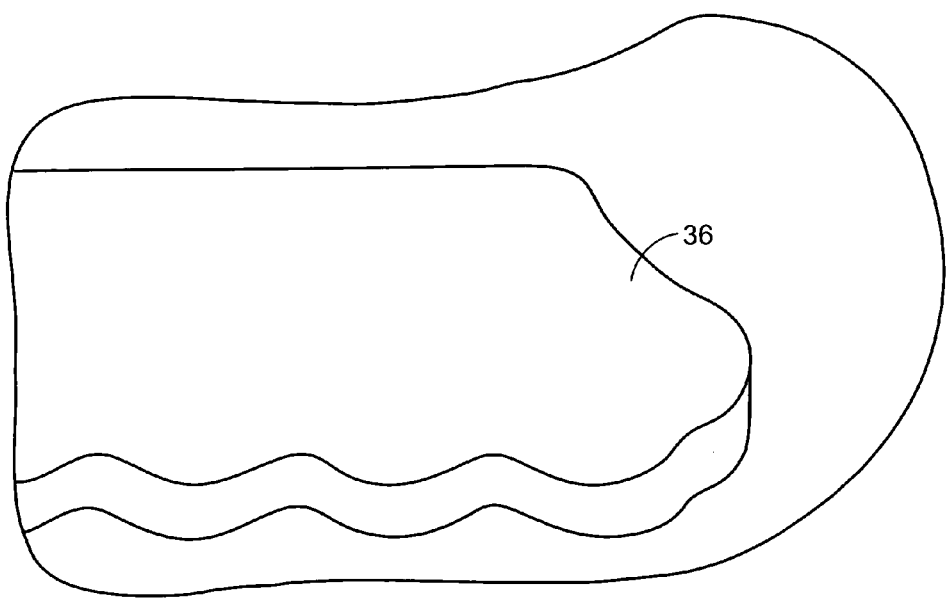

FIG. 5A and FIG. 5B illustrate an example of one of the gaskets. For instance, FIG. 5A and FIG. 5B are perspective views of a portion of the first gasket 36 of FIG. 2. FIG. 5A is a perspective view of the first gasket 36. FIG. 5B is a perspective view of the first gasket 36 shown in FIG. 5A looking at toward a side of the first gasket 36 that opposes the side shown in FIG. 5A. The illustrated first gasket 36 is formed of a single layer of material although the first gasket 36 can have a multi-layer construction and/or a multi-material construction. The valve recesses 38 and chamber recesses 52 each extend part way into the common region.

Figure 6A:
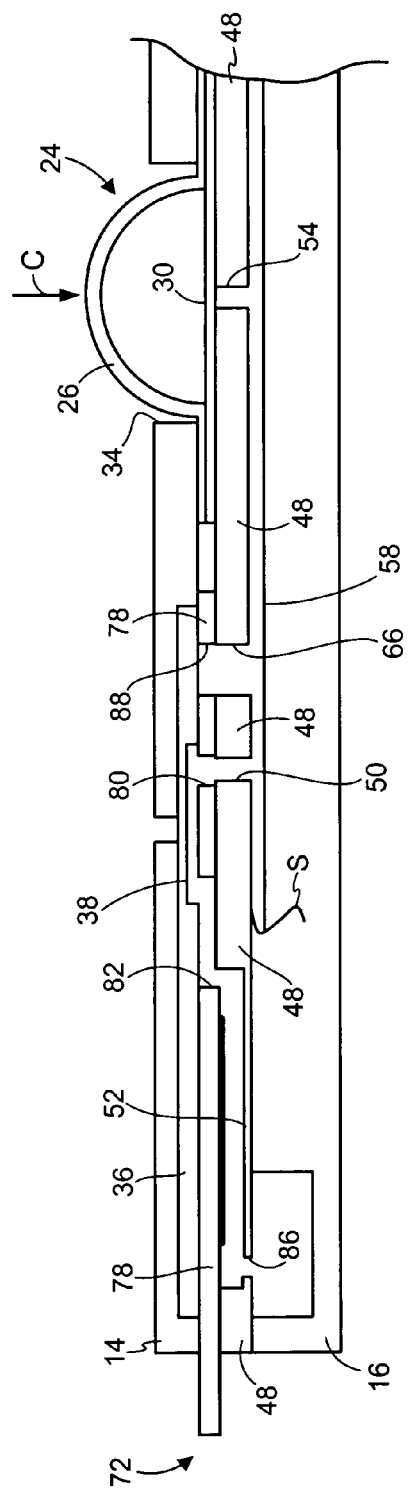
FIG. 6A and FIG. 6B illustrate operation of a cartridge constructed according to FIG. 1A through FIG. 1C.
Figure 6B:
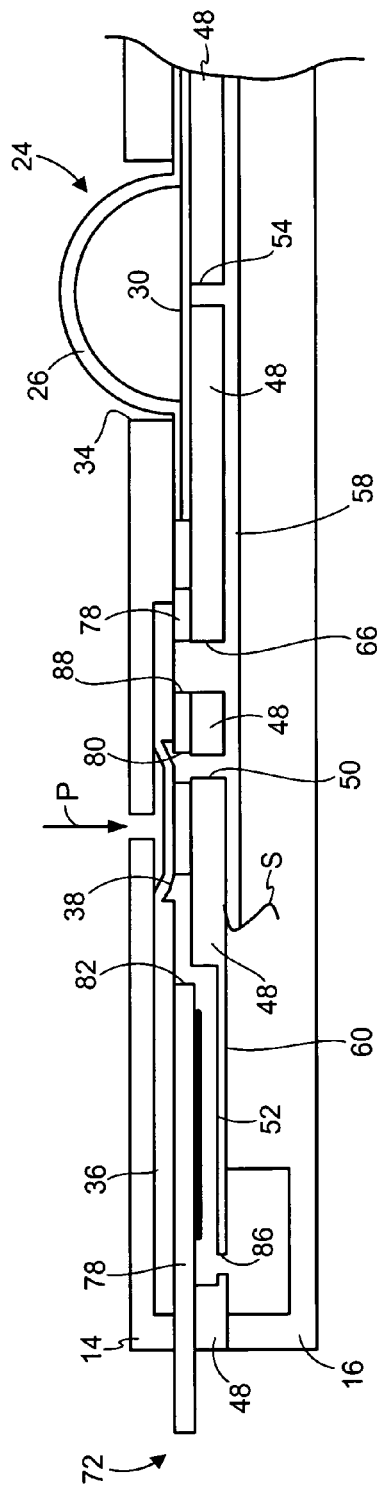

FIG. 6A and FIG. 6B illustrate operation of a cartridge constructed according to FIG. 1A through FIG. 1C. For instance, FIG. 6A and FIG. 6B illustrate the pathway that a liquid can flow from one of the reservoirs, into contact with one of the sensors 76, and into a waste reservoir 62. FIG. 6A and FIG. 6B is essentially a cross-section of the cartridge with the clamp 10 in the closed position, however, since the liquid flows through the cartridge in three dimensions, the cross-section is not taken along a plane but is instead taken along the liquid pathway from one of the reservoirs to one of the sensors 76, and then into one of the waste reservoirs 62. For the purposes of illustration FIG. 6A and FIG. 6B illustrate a single one of the reservoirs on the cartridge, a single one of the sensors 76, and a single one of the waster reservoirs although the cartridge can include more than one of these components.

During the operation of the cartridge, the cartridge is inserted into a machine (not shown) that can perform the assay. The machine can initiate the transport of a liquid in one of the reservoirs to one of the sensors 76 by compressing the reservoirs as shown by the arrow labeled C in FIG. 6A. The compression of the reservoir can be mechanical, hydraulic and/or pneumatic. The compression of the reservoir drives liquid in the reservoir through the septum 30 and then through the reservoir opening 54 in the second gasket 48. The liquid can enter the common channel 58 from the reservoir opening 54. As is evident in FIG. 6A, a portion of the liquid conduit that is partially defined by the common channel 58 is also partially defined by the second gasket 48.

The liquid flows along the common channel 58 past the gas opening 66 and the aligned secondary gas opening 88. The aligned gas opening 66 and secondary gas opening 88 act together to form a gas trap. For instance, gas and/or air bubbles in the liquid flowing past the gas trap can rise and enter the gas opening 66 and/or the secondary gas opening 88. As a result, the gas trap reduces the amount of air and/or gasses in the common channel 58.

The liquid flows past the gas trap and enters one or more of the valve openings 50 in the second gasket 48. For the purposes of illustration only one of the valve openings 50 is shown FIG. 6A, however, the line labeled S illustrates that the common channel 58 can carry the liquid to other valve openings 50 or to a vent discussed below.

Liquid that flows through a valve opening 50 can also flow through the second valve conduit 80 that is included in the sensor structure 72 and that is aligned with the valve opening 50. The liquid can then flow from the secondary valve conduit 80, into the valve recess 38 in the first gasket 36, and then into the valve specific channel in the sensor structure 72. As is evident in FIG. 6A, a portion of the liquid conduit partially defined by the valve specific channel is also defined by the first gasket 36 and the second gasket 48. The liquid can flow from the valve specific channel into the associated chamber recess 52 in the second gasket 48. As is evident from FIG. 6A, a portion of the functional chamber partially defined by the chamber recess 52 is also partially defined by a portion of the sensor structure 72. Additionally, one or more of the sensors 76 on the sensor structure 72 can be located in the functional chamber. For instance, FIG. 6A illustrates a working electrode 104 positioned in the functional chamber. The flow of the liquid into the chamber recess 52 and accordingly into the functional chamber brings the liquid into contact with the sensor 76 in the functional chamber. The liquid can flow from the functional chamber through the waste opening 86 in the second gasket 48 and into a waste reservoir 62 in the second shell 16. As a result, the pressure that is applied to the reservoir by the machine can drive the liquid into contact with the sensor 76 and into a waste reservoir 62.

The assembly of the components forms valves in the cartridge. FIG. 6A and FIG. 6B illustrate operation of one of these valves. For instance, as shown by the arrow labeled P in FIG. 6B, the machine can include a mechanism for increasing the pressure upon the bottom of the valve recess 38 through the aligned valve actuation opening 46 in the first shell 14. The mechanism for increasing the pressure can be mechanical, hydraulic, and/or pneumatic. For instance, the machine can include a manifold that can be employed to selectively deliver air into the aligned valve actuation opening 46. As is evident from a comparison of FIG. 6A to FIG. 6B, the increased pressure on the bottom of the valve recess 38 drives the bottom of the valve recess 38 against the substrate 78 on the sensor structure 72. As a result, the liquid pathway through the valve recess 38 is closed and the valve is accordingly closed. When the valve is closed, the liquid cannot flow from the common channel 58 into the functional chamber that receives liquid through the closed valve.

When the pressure applied to the bottom of the valve recess 38 is released, the liquid pathway through the valve recess 38 opens and the valve is accordingly opened as shown in FIG. 6A. When the valve is opened, the liquid can flow from the common channel 58 into the functional chamber that receives liquid through the closed valve. The machine can open and close the valves to control the flow of liquids into different functional chambers. For instance, the machine can cause the liquid in one of the reservoirs to be transported into contact with a particular sensor 76 by closing the valves associated with each of the other sensors 76.

Figure 7:
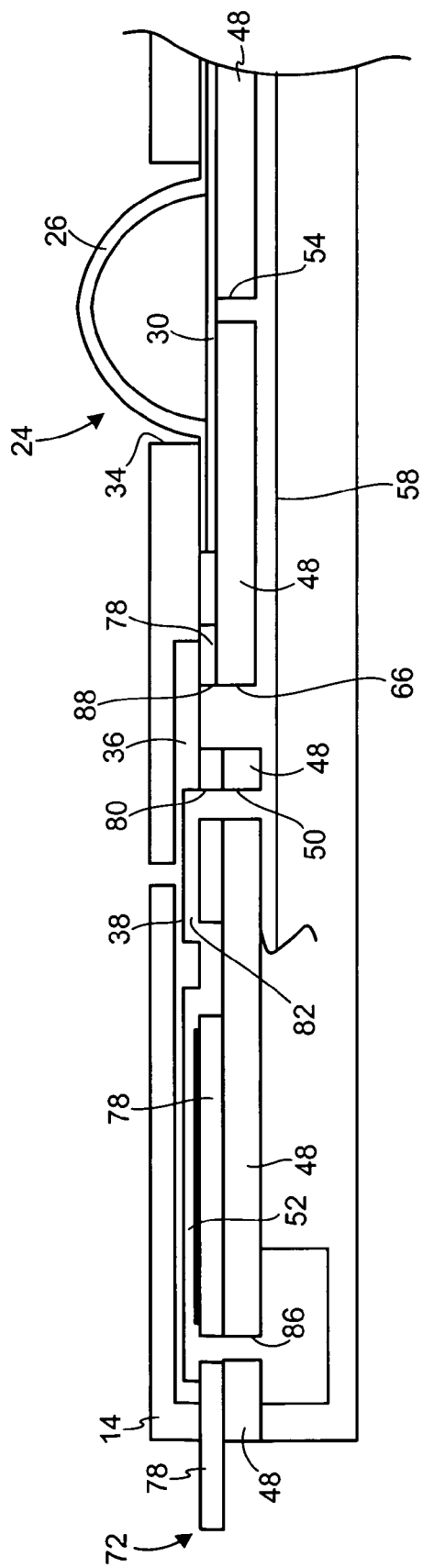
FIG. 7 illustrates operation of a cartridge constructed according to FIG. 2.

FIG. 7 illustrates operation of a cartridge constructed according to FIG. 2. For instance, FIG. 7 illustrates the pathway that a liquid can flow from one of the reservoirs, into contact with one of the sensors 76, and into a waste reservoir 62. FIG. 7 is essentially a cross-section of the cartridge with the clamp 10 in the closed position, however, since the liquid flows through the cartridge in three dimensions, the cross-section is not taken along a plane but is instead taken along the liquid pathway from one of the reservoirs to one of the sensors 76, and then into one of the waster reservoirs. For the purposes of illustration FIG. 7 illustrates a single one of the reservoirs on the cartridge, a single one of the sensors, and a single one of the waster reservoirs although the cartridge can include more than one of these components.

Compression of the reservoir drives liquid in the reservoir through the septum 30 and then through the reservoir opening 54 in the second gasket. The liquid can enter the common channel 58 from the reservoir opening 54. A portion of the liquid conduit that is partially defined by the common channel 58 is also partially defined by the second gasket 48.

The liquid flows along the common channel 58 past the gas opening 66 and the aligned secondary gas opening 88. The aligned gas opening 66 and secondary gas opening 88 act together to form a gas trap. For instance, gas and/or air bubbles in the liquid flowing past the gas trap can rise and enter the gas opening 66 and/or the secondary gas opening 88. As a result, the gas trap reduces the amount of air and/or gasses in the common channel 58.

The liquid flows past the gas trap and enters one or more of the valve openings 50 in the second gasket 48. For the purposes of illustration, only one of the valve openings 50 is shown FIG. 7; however, the line labeled S illustrates that the common channel 58 can carry the liquid to other valve openings 50 or to a vent discussed below.

Liquid that flows through a valve opening 50 can also flow through a secondary valve conduit 80 included in the sensor structure 72 and aligned with the valve opening 50. The liquid can then flow from the secondary valve conduit 80, into the valve recess 38 in the first gasket 36, and then into the valve specific channel in the sensor structure 72. As is evident in FIG. 7, a portion of the liquid conduit partially defined by the valve specific channel is also defined by the first gasket 36 and the second gasket 48. The liquid can flow from the valve specific channel into the associated chamber recess 52 in the first gasket 36. As is evident from FIG. 7, a portion of the functional chamber that is partially defined by the chamber recess 52 is also partially defined by a portion of the sensor structure 72. Additionally, one or more of the sensors 76 on the sensor structure 72 can be located in the functional chamber. For instance, FIG. 7 illustrates a working electrode 104 positioned in the functional chamber. The flow of the liquid into the chamber recess 52 and accordingly into the functional chamber brings the liquid into contact with the sensor 76 in the functional chamber. The liquid can flow from the functional chamber through the waste conduit 94 in the sensor structure 72 and then through the waste opening 86 in the second gasket 48 and into a waste reservoir 62 in the second shell 16. As a result, the pressure that is applied to the reservoir by the machine can drive the liquid into contact with the sensor 76 and into a waste reservoir 62.

As with FIG. 6A and FIG. 6B, the assembly of the components of FIG. 7 forms valves in the cartridge. FIG. 7 shows a valve that is constructed and operated according as described in the context of FIG. 6A and FIG. 6B. As a result, the machine can open and close the valves to control the flow of liquids into different functional chambers. For instance, the machine can cause the liquid in one of the reservoirs to be transported into contact with a particular sensor by closing the valves associated with each of the other sensors.

The cartridges of FIG. 1A through FIG. 2 include a vent that can be employed to prime the common channel 58 and/or to vent fluids from the common channel 58. FIG. 8A through FIG. 8B illustrate operation of the vent in a cartridge constructed according to FIG. 1A through FIG. 1C. For instance, FIG. 8A and FIG. 8B illustrate the pathway that a liquid can flow from one of the reservoirs, through the vent and into a waste reservoir 62. FIG. 8A and FIG. 8B are essentially cross-sections of the cartridge with the clamp 10 in the closed position; however, since the liquid flows through the cartridge in three dimensions, the cross-section is not taken along a plane but is instead taken along the liquid pathway from one of the reservoirs through the vent, and then into one of the waste reservoirs 62.

Compression of the reservoir drives liquid in the reservoir through the septum 30 and then through the reservoir opening 54 in the second gasket 48. The liquid can enter the common channel 58 from the reservoir opening 54. As is evident in FIG. 8A, a portion of the liquid conduit that is partially defined by the common channel 58 is also partially defined by the second gasket 48.

The liquid flows along the common channel 58 past the gas opening 66 and the aligned secondary gas opening 88 which act together to form a gas trap. The liquid flows past the gas trap and enters the vent inlet opening 68 in the second gasket 48. The line labeled S illustrates that the common channel 58 can also carry the liquid to other locations such as to valve openings 50 in the second gasket 48. The liquid that enters the vent inlet opening 68 in the second gasket 48 can flow through the vent inlet opening 68 and then through the secondary vent inlet opening 90 in the substrate 78 of the sensor structure 72. The liquid can then flow from the secondary vent inlet opening 90 into the vent recess 42 in the first gasket 36, and then into the secondary vent outlet opening 92 in the sensor structure 72. The liquid that enters the secondary vent outlet opening 92 can flow through the secondary vent outlet opening 92, through the vent outlet opening 70 in the second gasket 48, and into the aligned waste reservoir 62 in the second shell 16. Accordingly, compression of the reservoir can drive the liquid from the reservoir, through the vent and into a waster reservoir.

The vent includes a valve. The operation of the valve is shown in FIG. 8B. As shown by the arrow labeled P in FIG. 8B, the machine can include a mechanism for increasing the pressure upon the bottom of the vent recess 42 through the aligned valve actuation opening 46 in the first shell 14. The mechanism for increasing the pressure can be mechanical, hydraulic, and/or pneumatic. For instance, the machine can include a manifold that can be employed to selectively deliver air into the aligned valve actuation opening 46. As is evident from a comparison of FIG. 8A to FIG. 8B, the increased pressure on the bottom of the vent recess 42 drives the bottom of the vent recess 42 against the substrate 78 of the sensor structure 72. As a result, the liquid pathway through the vent is closed and the valve in the vent is accordingly closed. When the valve is closed, the liquid cannot flow from the common channel 58 and through the vent into a waste reservoir 62.

When the pressure applied to the bottom of the vent recess 42 is released, the liquid pathway through the vent opens and the valve is accordingly opened as shown in FIG. 8A. When the valve in the vent is opened, the liquid can flow from the common channel 58 and through the vent into a waste reservoir 62. The vent can be used during the priming of the cartridge and/or during the operation of the cartridge. For instance, during priming of the cartridge, the valves associated with each of the functional chambers can be closed and the valve in the vent can be opened. As a result, the liquid from one or more of the reservoirs can flow through the common channel 58 without entering an functional chamber. This mechanism can also be used to reduce the amount of air and/or gas in the common channel 58 before the liquids are transported into the functional chambers. During the transport of liquids into the functional chambers, the valve in the vent can be closed in order to reduce or stop the flow of the liquid through the vent.

Although operation and formation of the vent is disclosed in the context of the cartridge of FIG. 1A through FIG. 2, the vent also results from the assembly of the cartridge illustrated in FIG. 2.

Figure 9:
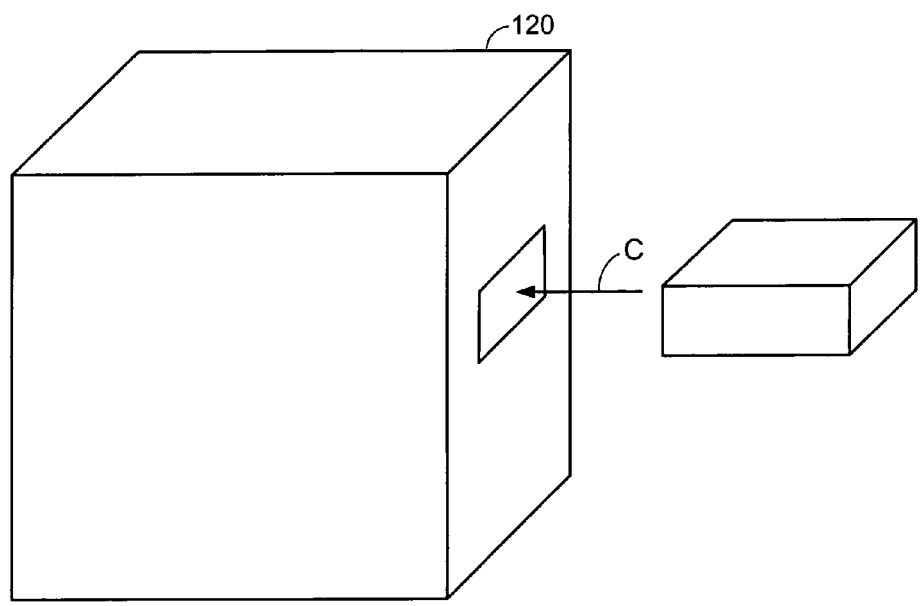
FIG. 9 illustrates a cartridge being inserted into a machine for operating the cartridge.

As noted above, the cartridge is inserted into a machine 120 as shown by the arrow labeled C in FIG. 9. The machine 120 can include electronics, mechanics, hydraulics, and/or pneumatics that perform the functions described above. Additionally, the machine can employ an inserted cartridge to perform an assay. For instance, the electrical contacts 108 on the sensor structure 72 can be exposed through the hinge 12 of the cartridge. The electronics in the machine can be in electrical communication with the electrical contacts 108 and accordingly with the electrodes included in the sensors. The machine can cause the appropriate series of liquids to be transported into contact with the appropriate sensors in a particular sequence. The liquids can include reagents, and solutions including wash solutions. The liquids can be transported into contact with the sensors such that a sample is formed on each of the sensors or on a portion of the sensors. The sample on different sensors can be the same or different. The machine can then operate the sensors so as to perform and assay on the samples. For instance, the machine can apply electrical energy to the electrodes of sensor constructed according to FIG. 4 so as to perform a cyclic voltammetry analysis on each of the samples.

Although the cartridge is disclosed in the context of a cartridge that has more than one reservoir and more then one sensor, a cartridge can be constructed with a single reservoir and/or a single functional chamber. Since each reservoir and functional chamber is associated with particular structures in the various components, changing the number of reservoirs and/or functional chambers can result in a change in the number of associated structures. For instance, when the cartridge includes a single reservoir, the second gasket 48 need include only a single reservoir opening 54 but can optionally include more. As another example, when the cartridge includes an functional chamber, the sensor structure 72 need include only a single sensor specific channel 82 but can optionally include more.

The use of different components that are not immobilized relative to one another allows the cartridge to be quickly customized to perform different assays. For instance, different components can be quickly fabricated and placed into the cartridge. As an example, the clamp can be constructed of polymers such and/or acrylic based materials. As a result, the clamp can be fabricated using three-dimensional printing technologies such as the three-dimensional printing technology available from Objet Geometries Ltd. of Billerica, Mass. and Rehovot, Israel. These technologies typically employ one or more computer controlled jets such as ink jets. The design of a three dimensional object is entered into the computer. The computer then operates the jet so as to form the three-dimensional object. The object is formed in layers. To form each layer, the jet sprays a liquid, such as photopolymer, through an inkjet-type printhead. In some instances, the layer is cured. For instance, the printhead can include an ultraviolet flood lamp that cures the layer. Other methods of fabricating the clamp can be employed. For instance, injection molding may be suitable for mass production of the clamp where three-dimensional printing may be suitable for prototyping.

Since the first gasket 36 and the second gasket 48 form a seal when pressed against other components of the cartridge, suitable materials for the first gasket 36 and the second gasket 48 include, but are not limited to, silicone, synthetic rubber, thermoplastic elastomers (TPE), and polyurethane. As a result, the gaskets can be cut from a sheet with a laser. The recesses and/or openings can also be formed with the laser using laser cutting and/or rasterization techniques. Since the laser can be computer controlled, these gaskets can generally be both designed and fabricated in short periods of time.

The ability to quickly design and fabricate the components of the cartridge allows the cartridge to be customized to different assays. For instance, the components of the cartridge can be changed such that the cartridge includes a different number of functional chambers, reservoirs, valves, vents, and/or channels for transporting liquids to and/or from these components. Additionally or alternately, the components of the cartridge can be changed such that the channels provide liquid communication between different features of the cartridge.

In one example, a first cartridge is used to perform a first assay. After performing the first assay, a second cartridge is used to perform a second assay. The second cartridge includes a portion or all of the components from the first cartridge but also includes components that were not included in the first cartridge. The components in the first and second cartridge include or consist of one, more than one, or all of the members of the group consisting of a clamp, a sensor structure, a first gasket, a second gasket, and a reservoir member. In some instances, the components that are included in the second cartridge but not included in the second cartridge have different features where the features of the components are described above. For instance, the reservoir member included in the first cartridge can have a different number of reservoirs than the reservoir member included in the second cartridge. Other examples of features include but are not limited to, recesses, conduits, openings, valves, vents, channels, and the number and/or layout of these features.

Another advantage of the cartridge construction is interchangeability of the different components. For instance, the cartridge can be included in a system that includes multiple first substitute components. Each of the first substitute components is interchangeable in that each of the first substitute components can be substituted for one of the components of the cartridge and the cartridge can then be assembled using the substitute components. For instance, each of the first substitute components can serve as the clamp in the cartridge, or each of the first substitute components can serve as the first gasket in the cartridge, or each of the first substitute components can serve as the second gasket in the cartridge, or each of the first substitute components can serve as the sensor structure in the cartridge. Further, each of the first substitute components can include different features from the other first substitute components. For instance, the first substitute components can each be a substitute sensor structure. Each of these substitute sensor structures can serve as the sensor structure of the cartridge in the sense that each of these sensor structures fits into the sensor recess 74 in the same way as the other sensor structures. Each of the substitute sensor structures can have different features. The features that are different are features that affect the functionality of the sensor structure. For instance, the difference in features can make different sensor structures suitable for use with different assays. Examples of different features include different devices. Different devices can include different types of devices and/or the same type of device but with different dimensions, sizes, shapes, sensitivity, etc. For instance, different devices can include different types of sensors and/or the same type of sensors with different dimensions. Different sensors can include different selections of coatings on the electrodes on the sensor structure. Different coatings include coatings having different compounds and/or coatings having different concentrations of the same compounds in the coatings. Examples of different coatings include coatings that include or consist of carboxylic, hydroxyl, biotin, streptavidin, dextran, antibodies, oligonucleotide probe solutions and also no coating as occurs with a bare gold electrode. Additional examples of different features include different sizes of sensors and different distances between electrodes. Since each of the substitute sensor structures can have different features, the interchangeability of the sensor structures does not necessarily mean that each of the sensor structures is suitable for use with the gaskets that are in the cartridge but that the cartridge can be assembled using each of the substitute sensor structures. As a result, when substitute components exist, matching components may need to be identified before the cartridge can be assembled in a functional form.

Further, the system can include more than one type of substitute components. For instance, the system can include includes multiple first substitute components and multiple second substitute components where the first substitute components are substitutes for a different one of the components than the second substitute components. As an example, the first substitute components can each be a clamp and can each be interchangeable with one another; and the second substitute components can each be a reservoir member and can each be interchangeable with one another.

In some instances, the cartridge is part of a system where each of the components includes multiple substitutes. For instance, the system includes multiple interchangeable clamps, multiple interchangeable first gaskets, multiple interchangeable reservoir members, multiple interchangeable second gaskets, and multiple interchangeable sensor structures where each of the substitute. Each of the components that can be substituted for one another includes different features from one another. The different features are features that affect the functionality of the cartridge. For instance, substitute clamps can have a different number of pocket openings, and/or pocket openings that for pockets of different volumes and/or common channels with different shapes and/or layouts and/or common channels with dimensions and/or different number of common channels. Substitute gaskets can be constructed with functional chambers of different sizes, different numbers and/or sizes of valves and/or different numbers and/or sizes. Additionally or alternately, substitute gaskets can be constructed to direct liquid flow in different patterns. Substitute sensor structures can include different selections of devices such as different electrophoretic devices or sensors, and/or different selections of coatings on the electrodes of the devices. Examples of different coatings on the electrodes include different compounds in the coatings, and/or different concentrations of the compounds in the coatings. Examples of different compounds for including in the coatings are carboxylic, hydroxyl, biotin, streptavidin, dextran, antibodies, oligonucleotide probe solutions and also no coating as occurs with a bare gold electrode. Examples of different devices include different types of device and the same type of device but with different geometries such as different distances between electrodes and/or with different locations relative to the functional chamber. Substitute sensor structures can include different selections of devices such as different electrophoretic devices or sensors, and/or different selections of coatings on the electrodes of the devices. Examples of different devices include different types of device and different distances between electrodes. Substitute reservoir members can include different numbers of reservoirs. Additionally or alternately, substitute reservoir members can include different selections of liquids stored in the reservoirs. Examples of different liquids reagents that can be stored in different reservoirs include, but are not limited to, liquid samples, lysis buffers, stabilization buffers, washing buffers, antibodies, oligonucleotide probes solutions, enzyme solutions, substrate solutions, electrolytes, standards, DI water, detergents, and ionic solutions.

The availability of multiple substitute components allows the cartridge to be customized to fit particular uses. For instance, the sensor structure that is suitable for a particular assay can be identified. Each of the possible gaskets may not work with each of the possible sensor structures. For instance, the gaskets may be suitable for use with a sensor structures that requires a different number of functional chambers. As a result, the gaskets and that operate with the identified sensor structure can also be identified. Additionally, the clamp and reservoir member that operates with the identified gaskets, sensor structure and assay can also be identified. Since the parts are interchangeable, the cartridge can be assembled with each of the identified components.

Although the cartridge is disclosed as having components that are independent of one another when the clamp 10 is open but can be immobilized relative to one another by compression of the clamp 10, in some instance, it may be desirable to permanently immobilize one of components relative to another one of the components. For instance, different components can be bonded to one another using adhesives, glues, heat seals, and other bonding techniques.

Although the sensor structure 72 is disclosed in the context of electrochemical sensors, the sensors can be other types of sensors. Further, the functional chambers can include more than one sensor. For instance, one or more of the functional chambers can include another type of sensor in addition to an electrochemical sensor.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A device, comprising:
multiple components that are independent from one another but are configured to be detachably coupled with one another so as to form a cartridge;
one of the components is a clamp that includes a first portion hinged to a second portion such that the clamp can occupy an open position or can occupy a closed position with other components between the first portion and the second portion and with the clamp holding the other components together, the other components being the components other than the clamp; and
the cartridge having one or more reservoirs, one or more functional chambers, and one or more channels configured to transport a liquid stored in at least one of the one or more reservoirs into the one or more functional chambers.

2. The device of claim 1, wherein the cartridge includes one or more valves that can be operated in a first state and a second state, the first state stopping flow of a liquid along a pathway that includes the valve and the second state allowing flow of the liquid along the pathway.

3. The device of claim 1, wherein the clamp is constructed in accordance with a clamp constructed with three dimensional printing.

4. The device of claim 1, wherein the clamp presses the other components together when the clamp is in the closed position with the clamp holding the other components together.

5. The device of claim 4, wherein
when the clamp is in the closed position with the clamp holding the other components together, two of the other components contact one another such that a transport channel is formed between the two components, the liquid transport channel configured to transport liquids during operation of the cartridge, and
when the clamp is in the closed position with the clamp holding the other components together the clamp presses the two components together such that a liquid seal is formed between the two components.

6. The device of claim 1, wherein at least a portion of the one or more chambers each includes one or more electrodes.

7. The device of claim 1, wherein at least a portion of the one or more chambers each includes a sensor.

8. The device of claim 7, wherein the sensor is an electrochemical sensor.

9. The device of claim 8, wherein each of the electrochemical sensors includes a reference electrode, a counter electrode, and a working electrode.

10. A system, comprising:
multiple components that are independent from one another but are configured to be detachably coupled with one another so as to form a cartridge having one or more reservoirs, one or more functional chambers and one or more channels configured to transport a liquid stored in at least one of the one or more reservoirs into the one or more functional chambers;
the components including clamp configured to hold other components together, the other components being the components other than the clamp; and
multiple first substitute components, each of the first substitute components includes one or more features that are different from features on each of the other first substitute components,
each of the first substitute component being interchangeable in that any one of the first substitute components can serve as a first one of the components.

11. The system of claim 10, further comprising:
multiple second substitute components, each of the second substitute components includes one or more features that are different from features on each of the other second substitute components,
each of the second substitute component being interchangeable in that any one of the second substitute components can serve as a second one of the components, the second one of the components being a different one of the components than the first one of the components.

12. The system of claim 10, wherein first substitute components are each a sensor structure that includes one or more sensors that each include an electrode having a coating and
the one or more features includes a coating in that a selection of the coatings in any one of the first substitute components is different from the selection of the coatings on each of the other first substitute components.

13. A system, comprising:
a first cartridge having one or more reservoirs and one or more sensors and being configured to transport a liquid from at least one of the reservoirs into contact with the one or more sensors,
the first cartridge being constructed from multiple components that are independent from one another but are configured to be detachably coupled with one another so as to form the first cartridge;
a second cartridge having one or more reservoirs and one or more sensors and being configured to transport a liquid from at least one of the reservoirs into contact with the one or more sensors,
the second cartridge being constructed from multiple second components that are independent from one another but are configured to be detachably coupled with one another so as to form the second cartridge; and
the second cartridge being formed at a later time than the first cartridge and the second components including a re-use component and a substitute component,
the substitute component being a component that was not included in the first cartridge, and
the re-use component being one of the components that was previously used in the first cartridge and being other than a clamp configured to hold together the components from the first cartridge.

14. The system of claim 13, wherein the re-use component is selected from a group consisting of a sensor structure, a gasket, and a member that includes one or more reservoirs.

15. The system of claim 14, wherein the substitute component replaces one of the prior components that was included in the first cartridge but has one or more different features than the replaced component.

16. The method of claim 15, wherein the one or more different features are at least one feature selected from a group consisting of a recess, conduit, opening, valve, and channel.

17. A method, comprising:

forming a first cartridge having one or more reservoirs and one or more sensors and being configured to transport a liquid from at least one of the reservoirs into contact with the one or more sensors, the first cartridge being formed from multiple components that are independent from one another but are configured to be detachably coupled with one another so as to form the first cartridge; and detaching at least a portion of the components in the first cartridge and forming a second cartridge, the second cartridge having one or more reservoirs and one or more sensors and being configured to transport a liquid from at least one of the reservoirs into contact with the one or more sensors, the second cartridge being formed from multiple second components that are independent from one another but are configured to be detachably coupled with one another so as to form the second cartridge; and the second components including a re-use component and a substitute component, the substitute component being a component that was not included in the first cartridge, and the re-use component being one of the components that was previously used in the first cartridge and being other than a clamp configured to hold together the components from the first cartridge.

18. The device of claim 1, wherein one of the components is a reservoir member that includes multiple pockets and when the clamp is in the closed position with the other components between the first portion and the second portion, each of the pockets extends through the first portion of the clamp with the first portion of the clamp surrounding each of the pockets.

19. The device of claim 1, wherein the clamp includes a holding device configured to hold the clamp in the closed position with the other components between the first portion of the clamp and the second portion of the clamp and when the clamp is in the closed positioned, the holding device is positioned on an opposite side of the clamp from a hinge that hinges together the first portion of the clamp and the second portion of the clamp.

20. The device of claim 1, wherein the first portion is hinged to the second portion by a hinge on which the first portion and second portion can swing such that the first portion and the second portion move toward one another or the first portion and the second portion move away from one another.

* * * * *